(12) United States Patent
Bala et al.

(10) Patent No.: US 10,388,413 B2
(45) Date of Patent: Aug. 20, 2019

(54) INTELLIGENT ALERT SUPPRESSION

(71) Applicant: Cerner Innovation, Inc., Kansas City, KS (US)

(72) Inventors: Ramachandran Koduvayur Bala, Tirupati (IN); Damodar Reddy Karra, Bangalore (IN)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 16/019,080

(22) Filed: Jun. 26, 2018

(65) Prior Publication Data

US 2019/0066841 A1    Feb. 28, 2019

Related U.S. Application Data

(63) Continuation of application No. 15/131,231, filed on Apr. 18, 2016, now Pat. No. 10,037,411.

(30) Foreign Application Priority Data

Dec. 30, 2015    (IN) .......................... 4318/DEL/2015

(51) Int. Cl.
*G16H 40/67* (2018.01)
*G06F 19/00* (2018.01)
*G16H 40/63* (2018.01)
*G16H 50/30* (2018.01)

(52) U.S. Cl.
CPC ............ *G16H 40/67* (2018.01); *G06F 19/00* (2013.01); *G06F 19/3418* (2013.01); *G16H 40/63* (2018.01); *G16H 50/30* (2018.01)

(58) Field of Classification Search
CPC ... A61B 19/3418; G08B 25/001; G16H 40/67

USPC .......................................................... 340/501
See application file for complete search history.

(56) References Cited

U.S. PATENT DOCUMENTS

| | | |
|---|---|---|
| 4,237,344 A | 12/1980 | Moore |
| 5,319,355 A | 6/1994 | Russek |
| 5,319,363 A | 6/1994 | Welch et al. |
| 5,534,851 A | 7/1996 | Russek |
| 5,942,986 A | 8/1999 | Shabot et al. |

(Continued)

OTHER PUBLICATIONS

"Arc Solutions and EXTENSION, Inc. Announce New Collaboration Software Solutions, Specifically Designed for the Healthcare Sector", Press Release by Extension Healthcare, Jan. 7, 2010.

(Continued)

*Primary Examiner* — Eric Blount
(74) *Attorney, Agent, or Firm* — Shook, Hardy & Bacon, L.L.P.

(57) ABSTRACT

Methods, systems, and computer-readable media are provided for intelligent suppression of alerts. Alerts may be evaluated prior to presentation to determine whether to present the alert or suppress the alert to reduce alert fatigue. The evaluation includes analysis of the alert including specific alert parameters. Alert parameters include, but are not limited to, an age of the patient, one or more diagnoses of the patient, one or more problems of the patient, etc. Additional parameters that may be evaluated include an alert severity score, a threshold value, and an override rate. Alerts that qualify may be suppressed and the suppressed alerts may be provided as non-interruptive alerts (i.e., alerts that may be presented but do not require action in order to continue with a workflow).

20 Claims, 5 Drawing Sheets

(56) References Cited

U.S. PATENT DOCUMENTS

| | | |
|---|---|---|
| 5,999,846 A | 12/1999 | Pardey et al. |
| 6,754,516 B2 | 6/2004 | Mannheimer |
| 6,804,656 B1 | 10/2004 | Rosenfeld et al. |
| 6,928,370 B2 | 8/2005 | Anuzis et al. |
| 7,035,622 B2 | 4/2006 | Pappalardo et al. |
| 7,035,623 B2 | 4/2006 | Pappalardo et al. |
| 7,090,053 B2 | 8/2006 | Bothwell et al. |
| 7,123,950 B2 | 10/2006 | Mannheimer |
| 7,215,945 B2 | 5/2007 | Pappalardo et al. |
| 7,224,281 B2 | 5/2007 | Santoso et al. |
| 7,225,408 B2 | 5/2007 | O'Rourke |
| 7,249,036 B2 | 7/2007 | Bayne |
| 7,256,708 B2 | 8/2007 | Rosenfeld et al. |
| 7,307,543 B2 | 12/2007 | Rosenfeld et al. |
| 7,315,825 B2 | 1/2008 | Rosenfeld et al. |
| 7,321,862 B2 | 1/2008 | Rosenfeld et al. |
| D577,734 S | 9/2008 | Ryu et al. |
| 7,430,692 B2 | 9/2008 | White, III et al. |
| 7,454,359 B2 | 11/2008 | Rosenfeld et al. |
| 7,475,019 B2 | 1/2009 | Rosenfeld et al. |
| D599,812 S | 9/2009 | Hirsch |
| D599,813 S | 9/2009 | Hirsch |
| D607,004 S | 12/2009 | Kordus et al. |
| D625,317 S | 10/2010 | Jewitt et al. |
| D631,891 S | 2/2011 | Vance et al. |
| D640,276 S | 6/2011 | Woo |
| 7,981,032 B2 | 7/2011 | Santoso et al. |
| 8,015,030 B2 | 9/2011 | Brown |
| 8,092,380 B2 | 1/2012 | Rothman et al. |
| 8,100,829 B2 | 1/2012 | Rothman et al. |
| 8,122,006 B2 | 2/2012 | de Castro Alves et al. |
| 8,160,895 B2 | 4/2012 | Schmitt et al. |
| 8,165,893 B1 | 4/2012 | Goldberg et al. |
| 8,170,887 B2 | 5/2012 | Rosenfeld et al. |
| 8,175,895 B2 | 5/2012 | Rosenfeld et al. |
| D662,507 S | 6/2012 | Mori et al. |
| D665,399 S | 8/2012 | Carpenter et al. |
| 8,332,017 B2 | 12/2012 | Tarassenko et al. |
| 8,355,925 B2 | 1/2013 | Rothman et al. |
| 8,374,988 B2 | 2/2013 | Gawlick |
| 8,401,606 B2 | 3/2013 | Mannheimer |
| 8,401,607 B2 | 3/2013 | Mannheimer |
| 8,403,847 B2 | 3/2013 | Rothman et al. |
| 8,416,085 B2 | 4/2013 | Gawlick |
| 8,417,233 B2 | 4/2013 | Woloshyn |
| 8,417,662 B2 | 4/2013 | Gawlick |
| D682,294 S | 5/2013 | Kanalakis, Jr. et al. |
| D682,844 S | 5/2013 | Friedlander et al. |
| D682,858 S | 5/2013 | Frijlink |
| 8,451,101 B2 | 5/2013 | Somasundaram et al. |
| 8,454,506 B2 | 6/2013 | Rothman et al. |
| D686,221 S | 7/2013 | Brinda et al. |
| 8,543,534 B2 | 9/2013 | Alves et al. |
| D695,773 S | 12/2013 | Tagliabue et al. |
| D696,682 S | 12/2013 | Kim et al. |
| 8,615,291 B2 | 12/2013 | Moorman et al. |
| D700,914 S | 3/2014 | Jin et al. |
| D701,221 S | 3/2014 | Ahmed et al. |
| D705,239 S | 5/2014 | Thompson et al. |
| 8,775,196 B2 | 7/2014 | Simpson et al. |
| 8,838,196 B2 | 9/2014 | Mannheimer |
| 8,842,001 B2 | 9/2014 | Gilham et al. |
| D714,817 S | 10/2014 | Lee |
| D715,820 S | 10/2014 | Rebstock |
| D717,808 S | 11/2014 | Tsuru et al. |
| 8,886,663 B2 | 11/2014 | Gainsboro et al. |
| 8,886,792 B2 | 11/2014 | Biondi et al. |
| D719,577 S | 12/2014 | Tsuru et al. |
| D720,766 S | 1/2015 | Mandal et al. |
| 8,948,734 B2 | 2/2015 | Vaglio et al. |
| D733,175 S | 6/2015 | Bae |
| 9,052,809 B2 | 6/2015 | Vesto |
| D734,349 S | 7/2015 | Amin et al. |
| D734,350 S | 7/2015 | Inose et al. |
| D736,789 S | 8/2015 | Tursi et al. |
| 9,159,313 B2 | 10/2015 | Saeki et al. |
| D742,909 S | 11/2015 | Lee et al. |
| 9,185,202 B2 | 11/2015 | Herbst et al. |
| D747,343 S | 1/2016 | Brinda et al. |
| D751,097 S | 3/2016 | Sarafa et al. |
| D752,604 S | 3/2016 | Zhang |
| D752,614 S | 3/2016 | Kwon et al. |
| 9,280,637 B2 | 3/2016 | Vaglio et al. |
| D753,165 S | 4/2016 | Watson |
| D753,707 S | 4/2016 | Yang |
| D754,176 S | 4/2016 | Kim |
| D757,771 S | 5/2016 | Drozd et al. |
| D757,778 S | 5/2016 | Lemay |
| D758,386 S | 6/2016 | Zhang |
| D758,400 S | 6/2016 | Chang et al. |
| D759,687 S | 6/2016 | Chang et al. |
| D760,738 S | 7/2016 | Scalisi et al. |
| 9,400,874 B2 | 7/2016 | Powell et al. |
| D762,676 S | 8/2016 | Lim |
| D763,290 S | 8/2016 | Gupta et al. |
| D763,881 S | 8/2016 | Smith et al. |
| D763,882 S | 8/2016 | Liang |
| D764,511 S | 8/2016 | Han et al. |
| D765,110 S | 8/2016 | Liang |
| D766,294 S | 9/2016 | Smith |
| D767,605 S | 9/2016 | Mensinger et al. |
| 9,449,355 B2 | 9/2016 | Kozicki et al. |
| D770,491 S | 11/2016 | Jung |
| D771,667 S | 11/2016 | Woo |
| D771,670 S | 11/2016 | Chan et al. |
| D772,259 S | 11/2016 | Pahwa et al. |
| D775,167 S | 12/2016 | Vazquez |
| D777,184 S | 1/2017 | Yang et al. |
| D777,758 S | 1/2017 | Kisselev et al. |
| D778,929 S | 2/2017 | Mensinger et al. |
| D779,517 S | 2/2017 | Pierson et al. |
| D780,191 S | 2/2017 | Kelley |
| 9,582,978 B2 | 2/2017 | Herbst et al. |
| D781,315 S | 3/2017 | Wang |
| D784,384 S | 4/2017 | Hong et al. |
| D785,003 S | 4/2017 | Yun et al. |
| D785,008 S | 4/2017 | Lim et al. |
| D785,009 S | 4/2017 | Lim et al. |
| D785,012 S | 4/2017 | Jou |
| D785,029 S | 4/2017 | Gedrich et al. |
| 9,626,479 B2 | 4/2017 | Zaleski |
| 9,659,482 B2 | 5/2017 | Yang et al. |
| D789,947 S | 6/2017 | Sun |
| D789,949 S | 6/2017 | Sun |
| 9,706,966 B2 | 7/2017 | Colman et al. |
| 9,747,778 B2 | 8/2017 | Mukherji et al. |
| 9,805,573 B2 | 10/2017 | Herbst et al. |
| 9,836,940 B2 | 12/2017 | Herbst et al. |
| 9,881,475 B2 | 1/2018 | Herbst et al. |
| 9,911,300 B2 | 3/2018 | Herbst et al. |
| 9,924,908 B2 | 3/2018 | Hubert et al. |
| 2002/0040282 A1 | 4/2002 | Bailey et al. |
| 2003/0163789 A1 | 8/2003 | Blomquist |
| 2003/0191730 A1 | 10/2003 | Adkins et al. |
| 2004/0073453 A1 | 4/2004 | Nenov et al. |
| 2005/0065817 A1 | 3/2005 | Mihai et al. |
| 2005/0146431 A1 | 7/2005 | Hastings et al. |
| 2005/0151640 A1 | 7/2005 | Hastings |
| 2006/0049936 A1 | 3/2006 | Collins, Jr. et al. |
| 2006/0161457 A1 | 7/2006 | Rapaport et al. |
| 2007/0239488 A1 | 10/2007 | DeRosso |
| 2008/0021709 A1 | 1/2008 | Greer |
| 2008/0027288 A1 | 1/2008 | Renz |
| 2008/0074951 A1 | 3/2008 | Hubicki |
| 2009/0048868 A1 | 2/2009 | Portnoy et al. |
| 2010/0001838 A1 | 1/2010 | Miodownik et al. |
| 2010/0123587 A1 | 5/2010 | Walls |
| 2010/0137693 A1 | 6/2010 | Porras et al. |
| 2010/0223071 A1 | 9/2010 | Kland et al. |
| 2011/0001605 A1 | 1/2011 | Kiani et al. |
| 2011/0054946 A1 | 3/2011 | Coulter et al. |
| 2011/0106560 A1 | 5/2011 | Eaton, Jr. et al. |
| 2011/0196306 A1 | 8/2011 | De La Huerga |
| 2011/0208816 A1 | 8/2011 | Chavez |

(56) References Cited

U.S. PATENT DOCUMENTS

| | | |
|---|---|---|
| 2011/0295621 A1 | 12/2011 | Farooq et al. |
| 2012/0075103 A1 | 3/2012 | Powell et al. |
| 2012/0101847 A1 | 4/2012 | Johnson et al. |
| 2012/0169467 A1 | 7/2012 | Condra |
| 2012/0278104 A1 | 11/2012 | Traughber et al. |
| 2012/0284040 A1 | 11/2012 | Dupin |
| 2013/0009783 A1 | 1/2013 | Tran |
| 2013/0049950 A1 | 2/2013 | Wohlert |
| 2013/0065569 A1 | 3/2013 | Leipzig et al. |
| 2013/0085765 A1 | 4/2013 | Tuchinda et al. |
| 2013/0085798 A1 | 4/2013 | Spatola et al. |
| 2013/0096953 A1 | 4/2013 | Beverly et al. |
| 2013/0103768 A1 | 4/2013 | Freebeck |
| 2013/0104077 A1 | 4/2013 | Felt |
| 2013/0162424 A1 | 6/2013 | Treacy |
| 2013/0183923 A1 | 7/2013 | Brackett et al. |
| 2013/0297348 A1 | 11/2013 | Cardoza et al. |
| 2014/0039351 A1 | 2/2014 | Mix et al. |
| 2014/0051399 A1 | 2/2014 | Walker et al. |
| 2014/0070939 A1 | 3/2014 | Halverson et al. |
| 2014/0085080 A1 | 3/2014 | Carnes |
| 2014/0097961 A1 | 4/2014 | Vaglio et al. |
| 2014/0099929 A1 | 4/2014 | Vaglio et al. |
| 2014/0100873 A1 | 4/2014 | Vaglio et al. |
| 2014/0132413 A1 | 5/2014 | Fox et al. |
| 2014/0172996 A1 | 6/2014 | Deeter et al. |
| 2014/0184408 A1 | 7/2014 | Herbst et al. |
| 2014/0358585 A1 | 12/2014 | Reiner |
| 2015/0081339 A1 | 3/2015 | Vaglio et al. |
| 2015/0137968 A1 | 5/2015 | Rusin et al. |
| 2015/0148617 A1 | 5/2015 | Friedman |
| 2015/0254957 A1 | 9/2015 | Wilson et al. |
| 2016/0027277 A1 | 1/2016 | Herbst et al. |
| 2016/0110040 A1 | 4/2016 | Vaglio et al. |
| 2016/0360160 A1 | 12/2016 | Eizenberg |
| 2017/0024091 A1 | 1/2017 | Hosier, Jr. |
| 2017/0032093 A1 | 2/2017 | Norton et al. |
| 2017/0098037 A1 | 4/2017 | Agassi et al. |
| 2017/0109018 A1 | 4/2017 | Vaglio et al. |
| 2017/0109989 A1 | 4/2017 | Herbst et al. |
| 2017/0193801 A1 | 7/2017 | Bala et al. |
| 2017/0265819 A1 | 9/2017 | Colman et al. |
| 2017/0287300 A1 | 10/2017 | Herbst et al. |
| 2017/0352237 A1 | 12/2017 | Herbst et al. |
| 2017/0352238 A1 | 12/2017 | Herbst et al. |
| 2018/0102036 A1 | 4/2018 | Herbst et al. |
| 2018/0110477 A1 | 4/2018 | Collins, Jr. et al. |
| 2018/0144598 A1 | 5/2018 | Herbst et al. |
| 2018/0153455 A1 | 6/2018 | Guazzi et al. |
| 2018/0315428 A1 | 11/2018 | Johnson et al. |

OTHER PUBLICATIONS

"Clinical Workflow Solutions EXTENSION Health Alert", brochure published by NEC Corporation Sep. 17, 2012, Sep. 17, 2012, 8 pages.

"Contactive—A Caller ID App that Showcases Android's Openess", Available at: <http://techdomino.com/contactive-a-caller-id-app-that-showcases-androids-openess/>, Apr. 24, 2017, 3 pages.

Corrected Notice of Allowance received for U.S. Appl. No. 15/131,231, dated Jun. 8, 2018, 2 pages.

Detraz, Jerome, "Find and replace pop-up window", Available at: <https://web.archive.org/web/20130717090053/https://www.sketchappsources.com/free-source/190-find-replace-pop-up-window.html>, Jul. 17, 2013.

"ExDialer—Dialer & Contacts, Modoohut Communication, Android Apps on Google Play Accessed", Available at: <https://play.google.com/store/apps/details?id=com.modoohut.dialer&hl=en>, Apr. 24, 2017, 3 pages.

"Extension Mobile for Enterprise Healthcare Organizations Now Available on Apple iPhone and iPod Touch Via Apple AppStore", Available at: <http://www.extensionhealthcare.com>, Extension, Inc., Fort Wayne, Jan. 10, 2011, 2 pages.

"Extension, Inc. and AeroScout Partner to Deliver Solutions for Healthcare RTLS and VoiP", Available at: <http://www.extensionhealthcare.com>, Extension, Inc., Fort Wayne,Feb. 19, 2010, 2 pages.

"Extension, Inc. Launches New Interactive Communications Solution", Available at: <http://www.extensionhealthcare.com>, Extension,Inc., Fort Wayne, May 25, 2011, 3 pages.

Final Office Action received for U.S. Appl. No. 13/711,177, dated Feb. 20, 2015, 11 pages.

Final Office Action received for U.S. Appl. No. 13/711,206, dated Jul. 27, 2017, 12 pages.

Final Office Action received for U.S. Appl. No. 13/711,206, dated Nov. 3, 2016, 20 pages.

Final Office Action received for U.S. Appl. No. 13/711,206, dated Oct. 2, 2015, 15 pages.

Final Office Action received for U.S. Appl. No. 13/711,217, dated Jun. 19, 2014, 8 pages.

Final Office Action received for U.S. Appl. No. 14/551,555, dated Jan. 23, 2018, 18 pages.

Final Office Action received for U.S. Appl. No. 29/602,910, dated Mar. 2, 2018, 13 pages.

First Action Interview Office Action received for U.S. Appl. No. 13/711,206, dated Mar. 17, 2015, 5 pages.

First Action Interview Office Action received for U.S. Appl. No. 14/551,555, dated Aug. 9, 2017, 6 pages.

How to create a cool and usable CSS3 search box, Available at: <https://catalin.red/how-to-create-a-cool-and-usable-css3-search-box/>, Feb. 18, 2011.

"How to Design an iPhone App in Photoshop", Available at: <https://medialoot.com/blog/how-to-design-an-iphone-app-in-photoshop/>, Oct. 26, 2011, 23 pages.

"How to download Skype app on Android and do Voice and video chat", Available at: <http://www.howto-connect.com/how-to-download-skype-app-on-android-and-do-voice-and-video-chat/>, Oct. 29, 2012, 5 pages.

"How to Set Up Zoom on Android", Available at: <http://blog.recovery-android.com/set-up-zoom-in-android/>, Jan. 14, 2016, 3 pages.

Non-Final Office Action received for U.S. Appl. No. 13/711,177, dated Jul. 7, 2014, 12 pages.

Non-Final Office Action received for U.S. Appl. No. 13/711,177, dated Jul. 8, 2015, 5 pages.

Non-Final Office Action received for U.S. Appl. No. 13/711,206, dated Feb. 25, 2016, 17 pages.

Non-Final Office Action received for U.S. Appl. No. 13/711,206, dated Mar. 23, 2017, 10 pages.

Non-Final Office Action received for U.S. Appl. No. 13/711,217, dated Jan. 30, 2014, 8 pages.

Non-Final Office Action received for U.S. Appl. No. 14/875,800, dated Apr. 24, 2018, 22 pages.

Non-Final Office Action received for U.S. Appl. No. 14/877,808, dated Sep. 8, 2016, 7 pages.

Non-Final Office Action received for U.S. Appl. No. 15/630,617, dated Sep. 21, 2017, 7 pages.

Non-Final Office Action received for U.S. Appl. No. 29/602,910, dated Jul. 13, 2017, 14 pages.

Non-Final Office Action received for U.S. Appl. No. 13/731,191, dated Jun. 3, 2015, 4 pages.

Notice of Allowance received for U.S. Appl. No. 13/711,177, dated Oct. 29, 2015, 9 pages.

Notice of Allowance received for U.S. Appl. No. 13/711,217, dated Sep. 29, 2014, 7 pages.

Notice of Allowance received for U.S. Appl. No. 14/877,808, dated Jan. 5, 2017, 5 pages.

Notice of Allowance received for U.S. Appl. No. 15/131,231, dated Apr. 25, 2018, 5 pages.

Notice of Allowance received for U.S. Appl. No. 15/131,231, dated Jan. 30, 2018, 7 pages.

Notice of Allowance received for U.S. Appl. No. 15/392,926, dated Sep. 28, 2017, 7 pages.

Notice of Allowance received for U.S. Appl. No. 15/630,617, dated Oct. 30, 2017, 7 pages.

(56) References Cited

OTHER PUBLICATIONS

Notice of Allowance received for U.S. Appl. No. 15/684,563, dated Jan. 10, 2018, 5 pages.
Notice of Allowance received for U.S. Appl. No. 15/684,565, dated Dec. 19, 2017, 7 pages.
Notice of Allowance received for U.S. Appl. No. 29/602,800, dated Jul. 19, 2017, 15 pages.
Pre-Interview First Office Action received for U.S. Appl. No. 13/711,206, dated Sep. 25, 2014, 4 pages.
Pre-Interview First Office Action received for U.S. Appl. No. 13/731,191, dated Dec. 4, 2014, 4 pages.
Pre-Interview First Office Action received for U.S. Appl. No. 14/551,555, dated Apr. 13, 2017, 6 pages.
Pre-Interview First Office Action received for U.S. Appl. No. 15/131,231, dated Jun. 30, 2017, 4 pages.
Pre-Interview First Office Action received for U.S. Appl. No. 15/392,926, dated Aug. 17, 2017, 4 pages.
Pre-Interview First Office Action received for U.S. Appl. No. 15/684,563, dated Nov. 30, 2017, 4 pages.
Pre-Interview First Office Action received for U.S. Appl. No. 15/684,565, dated Nov. 15, 2017, 4 pages.
Review: Our Favourite Effective Contact Managers, Contaker Blog, Available at: <http://blog.contaker.com/?p=61>, Apr. 24, 2017, 6 pages.
Simon Ng, "How to Add Search Bar in Table View", Available at: <https://www.appcoda.com/how-to-add-search-bar-uitableview/>, Jul. 8, 2012.
"The American Hospital Association Endorses the Extension Healthid smart card system", Available at: <http://www.news-medical.net>, Aug. 21, 2009, 2 pages.
Final Office Action received for U.S. Appl. No. 14/875,800, dated Sep. 17, 2018, 20 pages.
Non-Final Office Action received for U.S. Appl. No. 15/837,856, dated Jul. 25, 2018, 7 pages.
Non-Final Office Action received for U.S. Appl. No. 15/290,443, dated Aug. 15, 2018, 7 pages.
Non-Final Office Action received for U.S. Appl. No. 14/551,555, dated Oct. 10, 2018, 29 pages.
Pre-Interview First Office Action received for U.S. Appl. No. 14/983,685, dated Jul. 6, 2018, 9 pages.
Riano, et al., "MPM: A Knowledge-based functional model of medical practice", Journal of Biomedical Informatics, vol. 46, No. 3, Jun. 2013, pp. 379-387.
Notice of Allowance received for U.S. Appl. No. 14/983,685, dated Mar. 12, 2019, 10 pages.
Final Office Action received for U.S. Appl. No. 14/551,555, dated May 16, 2019, 21 pages.

INTELLIGENT ALERT SUPPRESSION

CROSS-REFERENCE TO RELATED APPLICATIONS

This application is a continuation of U.S. application Ser. No. 15/131,231, filed Apr. 18, 2016, and entitled "INTELLIGENT ALERT SUPPRESSION," which claims a priority benefit under 35 U.S.C. § 119 to Indian Provisional Application No. 4318/DEL/2015, filed in India on Dec. 30, 2015 and entitled "INTELLIGENT ALERT SUPPRESSION," the entirety of which is incorporated by reference herein.

BACKGROUND

The adoption of Computerized Physician/Provider Order Entry (CPOE) systems in healthcare environments has offered many benefits to healthcare and effectively presented serious medication errors. However, alert fatigue is an unintended consequence of implementing CPOE systems. Alert fatigue is caused by an excessive number of alerts/warnings about items (e.g., Drug-drug/Drug-Allergy interactions, contraindications, dosages, etc.). As a result, providers may pay less attention to or even ignore vital alerts, thus limiting these systems' effectiveness which impacts patient care and safety. There is no current solution to counter alert fatigue by controlling the frequency of alerts or suppressing the alerts for a given patient and condition without having a negative impact on patient care and safety.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In brief and at a high level, this disclosure describes, among other things, methods, systems, and computer storage media for suppressing alerts. Alerts may be identified in a typical fashion (e.g., during use of a CPOE system) but are evaluated prior to presentation to determine whether to present the alert or suppress the alert. The evaluation includes analysis of the alert including specific alert parameters. Alert parameters include, but are not limited to, an age of the patient, a diagnosis of the patient, a problem of the patient, etc. Additional parameters that may be evaluated include an alert severity score, a threshold value, and an override rate. Alerts that qualify may be suppressed and the suppressed alerts may be provided as non-interruptive alerts (i.e., alerts that may be presented but do not require action in order to continue with a workflow).

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

In brief and at a high level, this disclosure describes, among other things, methods, systems, and computer storage media for suppressing alerts. Alerts may be identified in a typical fashion (e.g., during use of a CPOE system) but are evaluated prior to presentation to determine whether to present the alert or suppress the alert. The evaluation includes analysis of the alert including specific alert parameters. Alert parameters include, but are not limited to, an age of the patient, a diagnosis of the patient, a problem of the patient, etc. Additional parameters that may be evaluated include an alert severity score, a threshold value, and an override rate. Alerts that qualify may be suppressed and the suppressed alerts may be provided as non-interruptive alerts (i.e., alerts that may be presented but do not require action in order to continue with a workflow).

The claimed solution is necessarily rooted in computerized healthcare technology in order to overcome a problem specifically arising in the realm of computer healthcare information networks, and the claims address the problem of evaluating alerts to intelligently determine whether to present or suppress the alert. If adhering to the routine, conventional function of providing alerts, providers will continue to be overwhelmed with every alert that is generated and, thus, will continue to ignore a vast majority of alerts. Some surveys indicate that providers ignore 90% of alerts as they dismiss the alerts as obvious, resulting in ignoring high severity alerts and thereby causing patient safety concerns. The claimed invention provides a way to intelligently suppress alerts without compromising patient care and safety. It is not desirable to suppress all alerts so the right balance must be struck to alert adequately to prioritize patient safety. The claimed invention overcomes the limitations of current computer healthcare technology and provides other benefits that will become clear to those skilled in the art from the foregoing description.

Figure 1:
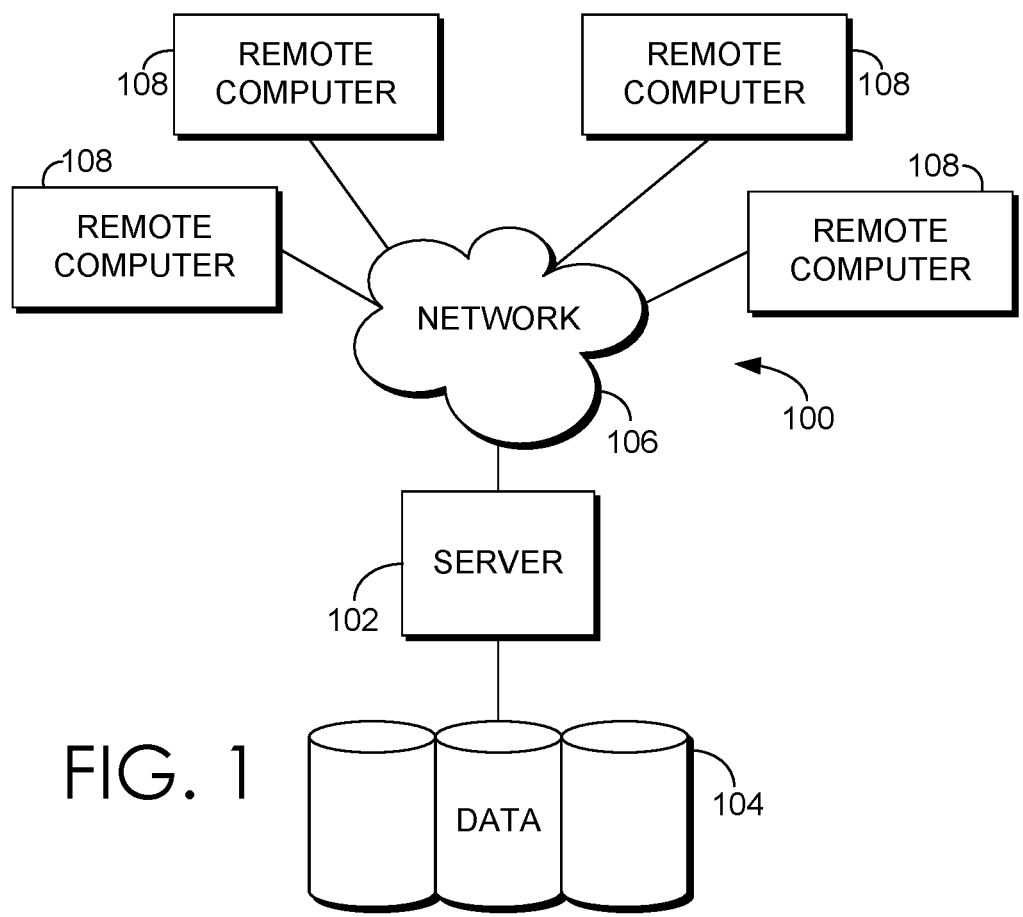
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known.

Accordingly, additional details concerning the internal construction of the control server 102 and the remote computers 108 are not further disclosed herein.

Figure 2:
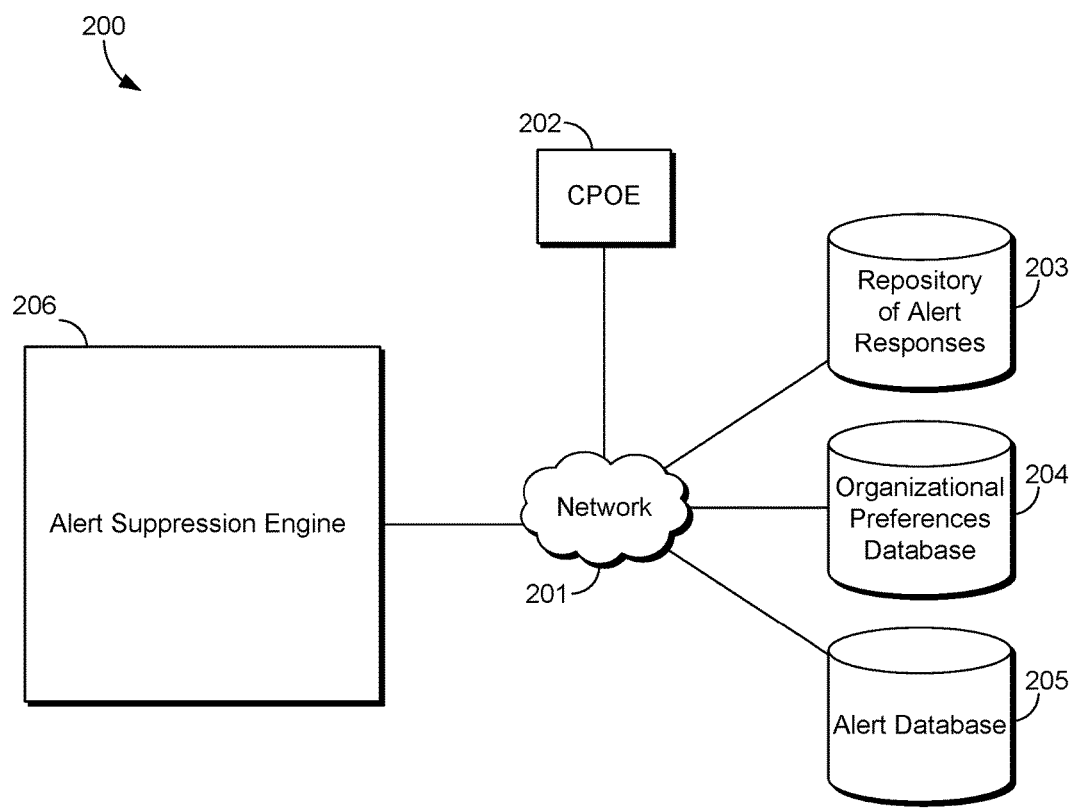
FIG. 2 is a block diagram of an exemplary system for suppressing alerts suitable to implement embodiments of the present invention.

Turning now to FIG. 2, a block diagram 200 is illustrated, in accordance with an embodiment of the present invention, showing an exemplary system for suppressing alerts. It will be understood and appreciated that the computing system shown in FIG. 2 is merely an example of one suitable computing system environment and is not intended to suggest any limitation as to the scope of the user or functionality of embodiments of the present invention. Neither should the computing system be interpreted as having any dependency or requirement related to any single component or combination of components illustrated therein. Further, although the various block of FIG. 2 are shown with lines for the sake of clarity, in reality, delineating various components is not so clear, and metaphorically, the lines would more accurately be grey and fuzzy. In addition, any number of physical machines (such as computing devices or portions of computing devices shown in FIG. 1), virtual machines, data centers, endpoints, or combinations thereof may be employed to achieve the desired functionality within the scope of embodiments of the present invention.

The components of FIG. 2 are capable of communicating with a number of different entities or data sources such as a repository for alert responses (RAR) 203, an organizational preferences database 204, and an alert database 205 for the collection of data. This communication may utilize, without limitation, one or more local area networks (LANs) and/or wide area networks (WANs). Such networking environments are commonplace in offices, enterprise-wide computer networks, intranets, and the Internet. Accordingly, the network 201 is not further described herein. As used throughout this application, the term "healthcare data" is meant to be broad and encompass any type of healthcare information. The healthcare data may be specific to a single patient or a group of patients. The healthcare data may also be directed to a clinician or group of clinicians. For example, healthcare data as it relates to a clinician may include patients that the clinician treats.

Returning now to FIG. 2, the exemplary system 200 includes a Computerized Provider Order Entry (CPOE) system 202, a repository of alert responses (RAR) 203, an organizational preferences database 204, an alert database 205, and an alert suppression engine (ASE) 206.

The CPOE system/device 202 may be any device configured as CPOE device. The CPOE device 202 is where providers input orders for patients. The CPOE device is where, in embodiments, alerts are originally generated. Alerts may be generated when a conflict is detected upon input of an order. However, utilizing the present invention, alerts are evaluated prior to presentation such that a determination whether to suppress the alert is made. When alerts are generated at the CPOE device 202, the alert is communicated to the ASE 206 along with patient contextual information such as a patient age, a patient diagnosis, and a patient problem. Additional information may also be communicated to the ASE 206 as discussed below. It is worth noting that while the CPOE device 202 and the ASE 206 are illustrated as separate components in FIG. 2, no such limitation is present in the invention as the ASE 206 may be, for instance, integrated into the CPOE device 202.

The RAR 203 is a knowledge base or collection of all past (historical) alert responses in the system 200. The RAR 203 may include previous alerts generated (presented and suppressed), frequency of particular alerts, how often the alert is overridden (i.e., override rate) by users, etc. Provided below is a sample of an exemplary RAR:

TABLE 1

Exemplary RAR records

| Alert Category | Alert Level | Override Rate (%) | Patient Age | Patient Diagnosis | Patient Problems |
|---|---|---|---|---|---|
| Contraindication | High | 75 | A | A12.345Z | 449890002 |
| Contraindication | Medium | 87 | B | A34.567P | 272060000 |
| Contraindication | Low | 96 | C | A56.789P | 224960004 |
| Drug-drug interaction | High | 73 | A | A12.345Z | 422627003 |
| Drug-drug interaction | Medium | 82 | C | A34.567P | 70944005 |
| Drug-drug interaction | Low | 90 | A | A56.789E | 282965002 |
| Dosage checking | High | 65 | B | A12.345Z | 449890002 |
| Dosage checking | Medium | 70 | D | A34.567P | 224960004 |
| Dosage checking | Low | 81 | E | A56.789E | 70944005 |

As shown in Table 1, each alert is associated with a category (e.g., contraindication, drug-drug interaction, etc.) and an alert level (e.g., high, medium, low, etc.). The alerts are also provided with patient contextual information such as age, diagnosis, and problems. The information may be extracted from a patient's electronic health record (EHR). The diagnosis and the problem may be stored as free text (e.g., a textual description of the diagnosis such as diabetes, superficial injury of the scalp, dislocation of the jaw, etc.) or it may be stored as a code (e.g., International Statistical Classification of Diseases and Related Health Problems (ICD) codes).

The organizational preferences database 204 may contain various preferences defined by an organization. Exemplary preferences include a threshold value/level for each category and level of alert. The system 200 may factor in a threshold value while suppressing the alerts. An exemplary organizational threshold level record is provided below in Table 2.

TABLE 2

| Alert Category | Alert Level | Threshold Value (%) |
|---|---|---|
| Contraindication | High | 100 |
| Contraindication | Medium | 95 |
| Contraindication | Low | 85 |
| Drug-drug interaction | High | 90 |
| Drug-drug interaction | Medium | 85 |
| Drug-drug interaction | Low | 75 |
| Dosage checking | High | 97 |
| Dosage checking | Medium | 85 |
| Dosage checking | Low | 80 |

The alert database 205 may be configured for, among other things, storing alert information. All alerts may be associated with an alert category. The organization of alerts and their associated categories may be stored in the alert database 205. Additionally, severity levels may be stored in the alert database 205 for corresponding alerts and alert categories. For example, a dosage check alert can have a severity level of high, medium, or low depending on the dosage that has been ordered.

The alert suppression engine (ASE) 206 may be configured for, among other things, determining when to suppress alerts. The ASE 206 may receive information from each of the above described data sources (i.e., the CPOE device 202, the RAR 203, the organizational preferences database 204, and the alert database 205). The ASE 206 may use any of the available information from the other components to arrive at patient-specific logic to suppress alerts for a given patient and condition. The main parameters utilized by the ASE 206 in the suppression determination include, but are not limited to, patient age, patient diagnoses, patient problems, alert severity scores, threshold values, and alert override rates. Each parameter may be assigned a weight, based on its impact on alerts. A sample worksheet is provided below in Table 3.

TABLE 3

| | | Weights | | | | | | |
|---|---|---|---|---|---|---|---|---|
| Alert Category | Alert Level | 15% Alert Severity Score | 15% Threshold Value (%) | 25% Override Rate (%) | 10% Patient Age Match (%) | 20% Patient Diagnoses Match (%) | 15% Patient Problems Match (%) | Weighted Average |
| Contraindication | High-3 | 3 | 100 | 75 | 0 | 25 | 50 | 0.49 |
| Contraindication | Med-2 | 2 | 95 | 87 | 100 | 50 | 70 | 0.70 |
| Contraindication | Low-1 | 1 | 85 | 96 | 100 | 30 | 60 | 0.65 |
| Drug-drug interaction | High-3 | 3 | 90 | 73 | 0 | 40 | 50 | 0.50 |
| Drug-drug interaction | Med-2 | 2 | 85 | 82 | 100 | 35 | 45 | 0.60 |
| Drug-drug interaction | Low-1 | 1 | 75 | 90 | 0 | 56 | 75 | 0.60 |
| Dosage checking | High-3 | 3 | 97 | 65 | 100 | 65 | 80 | 0.70 |
| Dosage checking | Med80-2 | 2 | 85 | 70 | 100 | 25 | 40 | 0.54 |
| Dosage checking | Low-1 | 1 | 80 | 81 | 0 | 50 | 30 | 0.48 |

Figure 3:
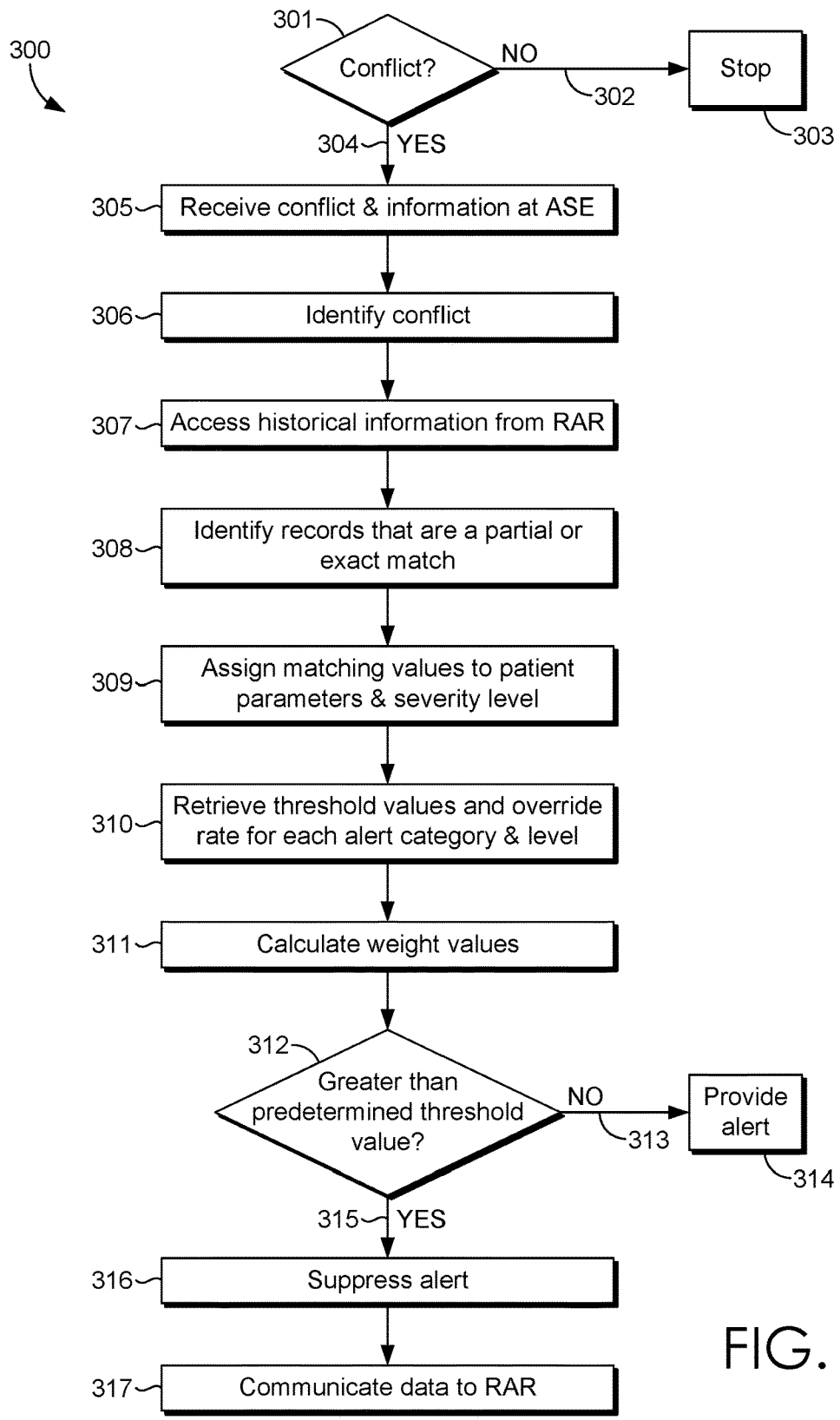
FIG. 3 is a flow diagram of an exemplary method of suppressing alerts in accordance with an embodiment of the present invention.

In application, the ASE 206 is invoked whenever there is a conflict in clinical checking while inputting an order (e.g., a test, a medication, etc.) through the CPOE 202 system. An exemplary embodiment is illustrated in FIG. 3 providing an exemplary method 300 for suppressing alerts. Initially, a determination that a conflict exists must be determined at block 301. If no conflict exists at step 302, the method stops at block 303. If a conflict is determined to exist at step 304, the information is communicated to the ASE 206 at block 305. The information communicated may include patient context information such as patient age, patient diagnoses, patient problems, and the like.

The ASE 206 then identifies the type of conflict at block 306. Types of conflicts include a category of alert/conflict, a severity associated with the category, and the like. Historical information is also accessed at block 307 from the RAR. The historical information accessed may be limited to information relevant to the patient context. For instance, if the alert is for a contraindication, only that category may be identified in the RAR. There is no need to evaluate all historical information in the RAR. Rather, patient context/parameters may be used to filter the records in the RAR. Once the information is accessed, records that are either a partial match or an exact match are identified at block 308. An exact match, as used herein, refers generally to a record that includes at least one item that exactly matches a patient parameter (e.g., a record for an alert of a patient that is 38 years old with a contraindication for Drug X matches an alert generated for a 38 year old for a contraindication for Drug X). Records that match exactly may be assigned values as shown below:
 Patient Age—100% (for exact matches found)
 Patient Diagnoses—100% (for exact matches found)
 Patient Problems—100% (for exact matches found)

A partial match, as used herein, refers generally to a record that includes information that partially matches that of the patient context information. Exemplary values are shown below:
 Patient Age—0%
 Patient Diagnoses—50% (based on number of matching diagnoses in patient context)
 Patient Problems—25% (based on number of matching problems in patient context)

The above described values are assigned to patient parameters at block 309 along with a severity level score. Each alert is associated with a severity level score (e.g., High—3, Medium—2, Low—1, etc.). That score is assigned at block 309. The ASE 206 may retrieve an override rate and a threshold value at block 310. The override rate indicates a history of overrides for a particular alert and the threshold value indicates an organizations preference for a threshold with which to measure when to suppress alerts and when to present alerts. The ASE 206 then calculates weight values at block 311. The weight values may be based on the percentages assigned to each parameter. The ASE 206 may use the calculated weight values and the threshold value to determine whether to suppress the alert. A decision block 312 indicates a decision of whether the weight value is greater than a threshold value is made. For instance, an organization preference (threshold value) may indicates that alerts are to be suppressed when a weight value is greater than 0.85. If the weight value is not greater than the threshold value at decision step 313, the alert is provided at block 314 as an un-suppressed alert (interruptive alert). Interruptive alerts are provided to users and block current actions until a response is received. A user needs to respond to an interruptive alert in order to continue with workflow. Users can either accept or reject the alert based on the context of treatment. The user responses may be communicated to the RAR for future analysis.

If it is determined at step 315 that the weight value is greater than the threshold value then the alert is suppressed at block 316. Suppressed alerts are non-interruptive alerts meaning that they do not block a user's actions or require a response in order to proceed with a workflow. The suppressed alert may be communicated to the RAR for future analysis at block 317. The suppressed alert is also available to the system 200 as a non-interruptive alert with no action required from the user for informational or regulatory purposes.

As is evidenced herein, the system 200 suppresses alerts based on patient context rather than suppressing based on generic manner override logic which does not take care of alerts specific to a patient. In other words, the system 200 intelligently suppresses alerts on a per-patient basis based on patient parameters. The intelligent suppression will reduce alert fatigue among providers and unnecessary workflow interruptions caused due to non-priority alerts.

Figure 4:
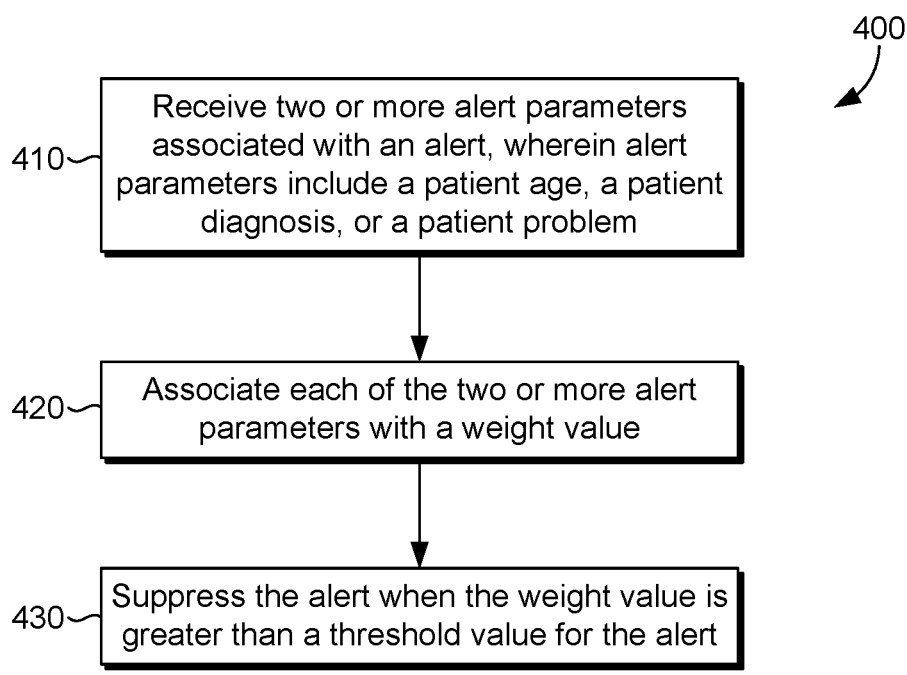
FIG. 4 is a flow diagram of an exemplary method of suppressing alerts in accordance with an embodiment of the present invention.

Turning now to FIG. 4, a flow diagram illustrating an exemplary method 400 is provided. Initially, at block 410, two or more alert parameters associated with an alert are received. The alert parameters may include a patient age, patient diagnoses, or a patient problem. At block 420, each of the two or more alert parameters is associated with a weight value. At block 430, the alert is suppressed when the weight value is greater than a threshold value for the alert.

Figure 5:
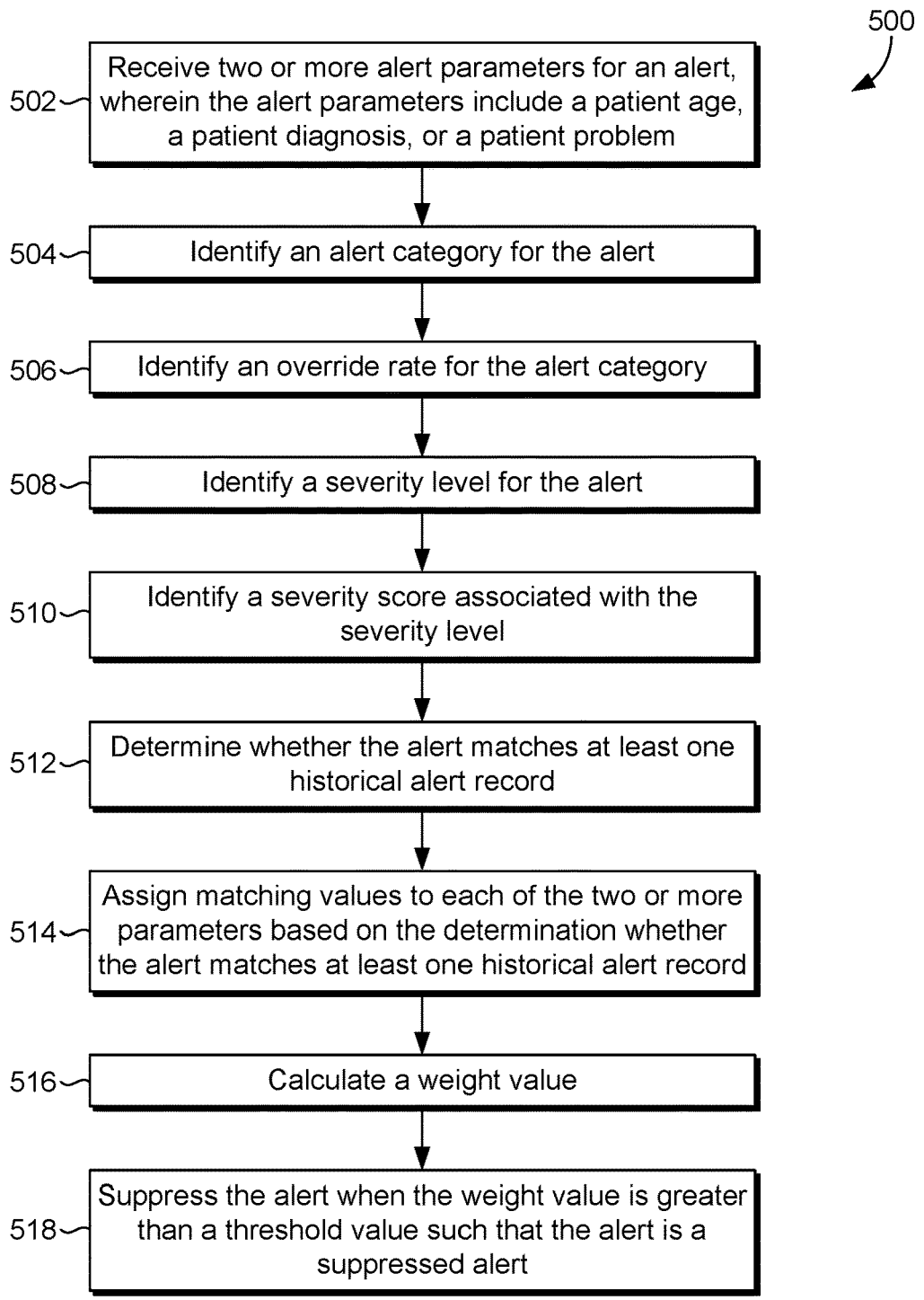
FIG. 5 is a flow diagram of an exemplary method of suppressing alerts in accordance with an embodiment of the present invention.

Turning now to FIG. 5, a flow diagram illustrating an exemplary method 500 is provided. Initially, at block 502, two or more alert parameters for an alert are received. The alert parameters may include a patient age, one or more patient diagnoses, or one or more patient problems. At block 504, an alert category for the alert is identified. At block 506, an override rate for the alert category is identified. At block 508, a severity level for the alert is identified. At block 510, a severity score associated with the severity level is identified. At block 512, a determination is made whether the alert matches at least one historical alert record. At block 514, matching values are assigned to each of the two or more parameters based on the determination whether the alert matches at least one historical alert record. At block 516, a weight value is calculated. At block 518, the alert is suppressed when the weight value is greater than a threshold value such that the alert is provided as a suppressed alert.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. An alert suppression engine comprising:
one or more processors; and
one or more computer storage media storing computer-executable instructions that, when executed by the one or more processors, implement a method comprising:
receiving healthcare data specific to at least one patient;
identifying at least two alert parameters associated with an alert, wherein the at least two alert parameters include at least one threshold value and a patient age;
analyzing the received healthcare data against the at least one threshold value;
based on the analyzing and the patient age, determining at least one additional alert parameter that includes a patient problem or a patient diagnosis;
identifying an alert category for the alert;
determining a severity level for the alert;
associating each of the at least two alert parameters and the at least one additional alert parameter with a weight value based on the severity level;
suppressing the alert when the weight value is greater than the threshold value for the alert; and
not suppressing the alert when the weight value is less than the threshold value for the alert and providing the alert to at least one remote computer, wherein the remote computer is a personal digital assistant.

2. The engine of claim 1, wherein the method further comprises determining a severity score for the alert.

3. The engine of claim 1, wherein the method further comprises identifying an override rate for the alert.

4. The engine of claim 1, wherein the method further comprises associating a matching value to the patient diagnoses, or the patient problem based on whether the patient diagnoses or the patient problem match historical alert information.

5. The engine of claim 4, wherein the matching value is a percent value.

6. The engine of claim 4, wherein the patient diagnoses or patient problem are identified as an exact match to historical alert information or a partial match to historical alert information.

7. The engine of claim 1, wherein the method further comprises communicating the alert and details regarding the suppression to a database.

8. The engine of claim 1, wherein the method further comprises providing a suppressed alert to the remote computer as a non-interruptive alert.

9. The engine of claim 1, wherein the method further comprises providing a non-suppressed alert as an interruptive alert.

10. The engine of claim 9, wherein the method further comprises receiving a response to the interruptive alert.

11. The engine of claim 1, wherein the method further comprises receiving a patient age.

12. An alert suppression engine comprising:
one or more processors; and
one or more computer storage media storing computer-executable instructions that, when executed by the one or more processors, implement a method comprising:
receiving healthcare data specific to at least one patient;
identifying at least two alert parameters associated with an alert, wherein the at least two alert parameters include at least one threshold value and a patient age;
analyzing the received healthcare data against the at least one threshold value;
based on the analyzing and the patient age, determining at least one additional alert parameter that includes a patient problem or a patient diagnosis;
determining a severity level for the alert;
associating the at least two alert parameters and the at least one additional alert parameter with a weight value based on the severity level;
suppressing the alert when the weight value is less than the threshold value for the alert;
not suppressing the alert when the weight value is greater than the threshold value for the alert and providing the alert to at least one remote computer, wherein the remote computer is a personal digital assistant; and
providing a suppressed alert to the remote computer as a non-interruptive alert.

13. The engine of claim 12, wherein the method further comprises determining a severity score for the alert.

14. The engine of claim 12, wherein the method further comprises identifying an override rate for the alert.

15. The engine of claim 12, wherein the method further comprises associating a matching value to the patient diagnoses, or the patient problem based on whether the patient diagnoses or the patient problem match historical alert information.

16. The engine of claim 12, wherein the method further comprises communicating the alert and details regarding the suppression to a database.

17. An alert suppression engine comprising:
one or more processors; and
one or more computer storage media storing computer-executable instructions that, when executed by the one or more processors, implement a method comprising:
receiving healthcare data specific to at least one patient;
identifying at least two alert parameters associated with an alert, wherein the at least two alert parameters include at least one threshold value and a patient age;
analyzing the received healthcare data against the at least one threshold value;
based on the analyzing and the patient age, determining at least one additional alert parameter that includes a patient problem or a patient diagnosis;
determining a severity level for the alert;
determining a severity score for the alert;
associating the at least two alert parameters and the at least one additional alert parameter with a weight value based on the severity level;
suppressing the alert when the weight value is less than the threshold value for the alert; and
not suppressing the alert when the weight value is greater than the threshold value for the alert and providing the alert to at least one remote computer, wherein the remote computer is a personal digital assistant.

18. The engine of claim 17, wherein the method further comprises communicating the alert and details regarding the suppression to a database.

19. The engine of claim 17, wherein the method further comprises providing a suppressed alert to the remote computer as a non-interruptive alert.

20. The engine of claim 17, wherein the method further comprises providing a non-suppressed alert as an interruptive alert.

* * * * *